United States Patent
Azizi et al.

(10) Patent No.: US 7,601,333 B2
(45) Date of Patent: Oct. 13, 2009

(54) USE OF A TETRAPEPTIDE ACSDKP (SEQ ID NO. 1) ANALOG RESISTANT TO THE ANGIOTENSIN I CONVERTING ENZYME FOR MEASURING GLOMERULAR FILTRATION RATE IN A HUMAN OR AN ANIMAL AND KIT CONTAINING SAME

(75) Inventors: Michel Azizi, Paris (FR); Eric Ezan, Malakoff (FR)

(73) Assignees: Assistance Publique-Hopitaux de Paris, Paris (FR); Commissariat a l'Energie Atomique, Paris (FR)

( * ) Notice: Subject to any disclaimer, the term of this patent is extended or adjusted under 35 U.S.C. 154(b) by 80 days.

(21) Appl. No.: 10/554,920

(22) PCT Filed: Apr. 28, 2004

(86) PCT No.: PCT/FR2004/001031

§ 371 (c)(1),
(2), (4) Date: Oct. 31, 2006

(87) PCT Pub. No.: WO2004/096292

PCT Pub. Date: Nov. 11, 2004

(65) Prior Publication Data

US 2008/0199397 A1  Aug. 21, 2008

(30) Foreign Application Priority Data

Apr. 29, 2003  (FR)  .................................. 03 05228

(51) Int. Cl.
*A61K 49/00* (2006.01)
*A61K 51/08* (2006.01)

(52) U.S. Cl. .......................... 424/9.1; 424/9.4; 530/330

(58) Field of Classification Search ....................... None
See application file for complete search history.

(56) References Cited

OTHER PUBLICATIONS

Junot, Christophe et al.: "Development of an enzyme immunoassay for a stable amidated analog of the hemoregulatory Peptide Acetyl-Ser-Asp-Lys-Pro", Journal of Immunoassay and Immunochemistry, vol. 22, No. 1, pp. 15-31, 2001.

Gaudron, Sandrine et al: "NAcSDKP Analogues Resistant to Angiotensin-Converting Enzyme", Journal of Medicinal Chemistry, vol. 40, pp. 3963-3968, 1997.

Azizi, Michel et al: "Renal and Metabolic Clearance of N-acetyl-seryl-aspartyl-lysyl-proline (AcSDKP) during angiotensin-converting enzyme Inhibition in humans", Hypertension (Baltimore), vol. 33, No. 3, pp. 879-886, 1999.

*Primary Examiner*—Jeffrey E Russel
(74) *Attorney, Agent, or Firm*—Oblon, Spivak, McClelland, Maier & Neustadt, L.L.P.

(57) ABSTRACT

The invention concerns the use of ACE-resistant N-acétyl-Ser-Asp-Lys-Pro analogues for preparing a reagent or marker adapted to measure a glomerular filtration rate.

14 Claims, 4 Drawing Sheets

| Acetyl | Ser *(CO-NH)* | Asp *(CO-NH)* | Lys *(CO-N)* | Pro | (AcSDKP) |
|---|---|---|---|---|---|
| Acetyl | Ser *(CH₂-NH)* | Asp | Lys | Pro | (SΨ) |
| Acetyl | Ser | Asp *(CH₂-NH)* | Lys | Pro | (DΨ) |
| Acetyl | Ser | Asp | Lys *(CH₂-N)* | Pro | (KΨ) |
| Acetyl | Ser | Asp | Lys | Pro-NH₂ | (AcSDKP-NH₂) |
| Acetyl | Ser | DAsp | Lys | Pro | (AcS_DDKP) |

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION ON NITROGEN

<400> SEQUENCE: 1

Ser Asp Lys Pro
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION ON NITROGEN
<220> FEATURE:
<221> NAME/KEY: MOD_RES
<222> LOCATION: (4)..(4)
<223> OTHER INFORMATION: AMINO GROUP COVALENTLY LINKED TO PROLINE
      NITROGEN

<400> SEQUENCE: 2

Ser Asp Lys Pro
1

USE OF A TETRAPEPTIDE ACSDKP (SEQ ID NO. 1) ANALOG RESISTANT TO THE ANGIOTENSIN I CONVERTING ENZYME FOR MEASURING GLOMERULAR FILTRATION RATE IN A HUMAN OR AN ANIMAL AND KIT CONTAINING SAME

The present invention relates to the measurement of glomerular filtration rate (GFR) in normal or sick humans and also in animals, by means of a novel method using an N-acetyl-Ser-Asp-Lys-Pro (ACSDKP) (SEQ ID NO: 1) tetrapeptide analog resistant to angiotensin I converting enzyme. The measurement of GFR makes it possible to accurately evaluate renal function; it constitutes an intermediate result in clinical practice, for thus identifying the beginnings of renal insufficiency and monitoring chronic renal insufficiency or renal insufficiency after kidney transplantation, in clinical practice. This fine evaluation of renal function is also essential for carrying out clinical research protocols and animal experimentation protocols.

The use of methods for accurately measuring GFR, overall indicator of kidney function, is essential because of the numerous limitations associated with estimating this physiological parameter only by means of creatinine clearance or by means of the blood creatinine value (endogenous marker) (Froissart M. et al., Medecine Nucléaire, 1995, 19, 263-276; Médecine Nucléaire, 1995, 19, 251-262). These measurements make use of glomerular filtration markers. Inulin remains the reference marker, but the methodological difficulties associated with its use limit the employment thereof to a small number of experienced teams (Froissart et al., mentioned above). Thus, the method consisting of the renal clearance of inulin maintained at a constant level, with urine collection, requires qualified and available personnel, the setting up of a continuous infusion, and iterative complete bladder emptying for each period, which is particularly difficult to implement in elderly individuals and young children. The calculation of clearance from the infusion rate of the marker or tracer, carried out in the equilibrium state, has a tendency to systematically overestimate the measurement of urinary clearance, due to the fact that inulin exits slowly into the interstitial extracellular sector, this being associated with poor diffusibility (Froissart et al. mentioned above). In addition, inulin is not very suitable for clearance methods after a single injection because it takes a considerable amount of time for the equilibrium state between the plasma and interstitial sectors to be reached. Finally, the use of inulin is limited by methodological constraints. Thus, dissolution by heating in a large volume is necessary before administration of inulin, and the assaying of inulin is based on a calorimetric method, which may pose a problem in the presence of chromogenic agents.

Labeled elements (radiopharmaceuticals) that are eliminated by glomerular filtration, such as $^{51}$Cr-EDTA, $^{99m}$Tc-DTPA or $^{125}$I-iothalamate, can also be used. The main advantage of radiopharmaceuticals is the accuracy with which they can be measured by counting both for blood samples and urine samples. Their many drawbacks reside in their cost, the need for a radioisotope laboratory, and the irradiation caused by their injection (Froissart et al., mentioned above).

Given the importance of the measurement of GFR in physiology, in pathology, in pharmacology, and in clinical and experimental research, and the limitations of the all the techniques at the disposal of the medical profession, the development of a novel glomerular filtration marker that is simple to use at the patient's bedside and at the same time allows a reliable measurement of GFR is justified.

A substance can be used as a marker or indicator for measuring GFR when it satisfies essentially the following criteria:
  of being able to be completely filtered by the glomerulus,
  of not being secreted, nor subsequently reabsorbed in the tubule,
  of not being metabolized when it passes through the kidney,
  of not having any physiological effect on kidney function,
  of not being bound to plasma proteins,
  of not being eliminated via an extrarenal route,
  of being devoid of toxicity, and
  of having a constant clearance for a wide plasma concentration range (Smith H. W. et al., Smith H W., ed. *Principles of renal physiology*. New York: Oxford University Press, 1957, 25-35).

Consequently, the applicant gave itself the aim of providing an indicator (marker or tracer) for glomerular filtration which satisfies the practical needs better and more readily than the indicators of the state of the art (inulin, creatinine or radiopharmaceuticals).

The hemoregulatory tetrapeptide N-acetyl-Ser-Asp-Lys-Pro (acetyl-SDKP or AcSDKP) (SEQ ID NO: 1) is a natural inhibitor of the entry of the murine hematopoietic stem cell into S-phase (Lenfant M. et al., Proc. Natl. Acad. Sci., 1989, 86, 779-782). In mice, exogenous administration of the peptide protects the medullary cells against the cytotoxic effects of anticancer drugs and of irradiation and significantly increases the survival of the animals treated (Masse A. et al., Blood, 1998, 91, 441-9). The biological properties of AcSDKP (SEQ ID NO: 1) allow in particular its use as a novel hematoprotective agent that can be used in vivo during antitumor chemotherapy and radiotherapy and also in vitro, as an adjuvant in bone marrow purging methods in the case of autografts in humans (see, for review, Azizi M. et al., Clin. Exp. Pharmacol. Physiol., 2001, 28, 1066-1069). The use of ACSDKP (SEQ ID NO: 1) in humans has necessitated the study of its stability in biological fluids. In vitro, angiotensin I converting enzyme (ACE), which has 2 homologous N- and C-terminal active sites and participates in the regulation of cardiovascular homeostasis, is the main enzyme involved in the catabolism of AcSDKP (SEQ ID NO: 1) (Rieger K. J. et al., Biochem. J., 1993, 296, 1-6). The N-terminal site of ACE is preferentially involved in hydrolysis of the peptide in vitro, since its catalytic effectiveness with respect to this substrate is 50 times greater than that of the C-terminal site (Rousseau A. et al., J. Biol. Chem., 1995, 270, 3656-3661). In humans, the AcSDKP (SEQ ID NO: 1) concentrations in the plasma and in the urine increase significantly during the acute or chronic inhibition of ACE (Azizi M. et al., J. Clin. Invest., 1996, 97, 839-844). The AcSDKP (SEQ ID NO: 1) is eliminated from the body via two mechanisms: firstly, hydrolysis by ACE and, secondly, glomerular filtration (Azizi M. et al., Hypertension, 1999, 33, 879-886). When ACE is active, the amount of AcSDKP (SEQ ID NO: 1) measured in the urine is low. It represents the residual amount of intact AcSDKP (SEQ ID NO: 1) which has not been degraded by the plasma and endothelial ACE and which is filtered in the glomeruli and then degraded by the ACE present at the surface of the proximal tubular cells. When the hydrolysis of the peptide is inhibited after administration of an ACE inhibitor, a massive increase is observed in urinary excretion of AcSDKP (SEQ ID NO: 1), which is associated with two mechanisms:
  with glomerular filtration of the free fraction of intact AcSDKP (SEQ ID NO: 1) in the plasma,
  and especially, with the inhibition of the tubular ACE by the inhibitor filtered in the glomerulus.

With an ACE inhibitor, the urinary clearance of AcSDKP (SEQ ID NO: 1) is increased but remains less than the endogenous creatinine clearance (69±27%) (Azizi M. et al., 1999, mentioned above). This difference is probably due to the sporadic nature of the degradation of the peptide by ACE between the doses of the inhibitor and not due to a tubular reabsorption of the peptide, since ACSDKP (SEQ ID NO: 1) is ionized at the urinary pH and weakly bound to the plasma proteins (<1%, Azizi M. et al., 1999, mentioned above). In fact, the AcSDKP (SEQ ID NO: 1) concentration in the plasma varies between a minimum value of 2 pmol/ml and a maximum value of 4 to 6 pmol/ml between two 50 mg doses of captopril, in a manner highly parallel with the inhibition of ACE, which oscillates between 60 and 99% between 2 doses (Azizi M. et al., 1999, mentioned above). The strictly parallel relationship between the evolution of the plasma concentrations of AcSDKP (SEQ ID NO: 1) and the activity of ACE clearly demonstrates an intermittent reactivation of ACE between two captopril doses. The exact contribution of the two mechanisms (renal clearance and intermittent reactivation of ACE) is clearly apparent in patients suffering from chronic renal insufficiency. Specifically, a predominant accumulation of ACSDKP (SEQ ID NO: 1) is observed in the plasma in patients suffering from renal insufficiency who are treated with an ACE inhibitor (Azizi M. et al., 1999, mentioned above). Patients suffering from renal insufficiency who are not treated with an ACE inhibitor show a discrete accumulation of the peptide in the plasma. In the course of terminal renal insufficency, two phenomena contribute to the massive increase in plasma concentrations of AcSDKP (SEQ ID NO: 1) in patients treated with an ACE inhibitor:

the peptide can no longer be eliminated by glomerular filtration, no intermittent reactivation of ACE can take place, due to the accumulation of the ACE inhibitor in the plasma and the tissues, in particular in patients receiving hemodialysis.

In the context of their previous studies, the inventors have in particular observed that AcSDKP (SEQ ID NO: 1) that is infused, in combination with ACE inhibitor, could serve as a marker for glomerular filtration (Azizi M. et al., J. Mol. Med., 2002, 80, 492-8). In the course of a study whose object was to evaluate the effects of insertion/deletion polymorphism of the ACE gene on AcSDKP (SEQ ID NO: 1) metabolism, the inventors gave normal volunteers, half of whom were receiving an ACE inhibitor, captopril at the dose of 50 mg 3 times/day for 3 days, and the other half of whom were receiving a placebo, an infusion of AcSDKP (SEQ ID NO: 1) at 1.12 µg/kg/min for 15 minutes (Azizi M. et al., 2002, mentioned above). Among the results obtained, the inventors show that with an ACE inhibitor, the urinary clearance of the exogenous peptide is very close to the glomerular filtration rate, estimated by means of the endogenous creatinine clearance. However, this procedure has the drawback of being complex, since the infusion of the peptide must be carried out at the peak of the ACE inhibition. In addition, there is also a substantial inter-individual variability of the ACE inhibition associated with variable bioavailability of the inhibitor.

The applicant has thus selected markers or indicators that satisfy the conditions stated above while at the same time not exhibiting the drawbacks of the prior methods described. It has been found, unexpectedly, that ACE-resistant analogs of the hemoregulatory tetrapeptide N-acetyl-Ser-Asp-Lys-Pro (AcSDKP) (SEQ ID NO: 1) are suitable for use as specific markers, tracers or indicators of glomerular filtration and thus satisfy the practical needs better than the methods previously used for measuring glomerular filtration rate.

Consequently, a subject of the present invention is the use of the ACE-resistant N-acetyl-Ser-Asp-Lys-Pro (SEQ ID NO: 1) analogs for preparing a reagent or tracer suitable for measuring GFR.

The ACE-resistant N-acetyl-Ser-Asp-Lys-Pro (SEQ ID NO: 1) analogs and the methods for preparing them are in particular described in the articles in the name of Gaudron S. et al. (Stem Cells, 1999, 17, 2, 100-106; J. Med. Chem., 1997, 40, 24, 3963-3968); these analogs are as follows:

three pseudopeptides, in which one of the peptide bonds has been replaced with an aminomethylene $\Psi(CH_2—NH)$ group:

N-acetyl-Ser($CH_2$—NH)-Asp-Lys-Pro: $S\Psi$
N-acetyl-Ser-Asp($CH_2$—NH)-Lys-Pro: $D\Psi$
N-acetyl-Ser-Asp-Lys($CH_2$—NH)-Pro: $K\Psi$ and a peptide modified at its C-terminal end by amidation: N-acetyl-Ser-Asp-Lys-Pro-$NH_2$ (SEQ ID NO: 2). This product differs from the initial molecule only through amidation of the carboxyl function of the proline residue located in C-terminal position of the peptide.

These various modifications confer, on said AcSDKP (SEQ ID NO: 1) analogs, great stability with respect to the hydrolysis induced by ACE.

In accordance with said use, said ACE-resistant N-acetyl-Ser-Asp-Lys-Pro (SEQ ID NO: 1) analogs are advantageously radiolabeled.

A subject of the present invention is also a method for measuring GFR, characterized in that it comprises determining the plasma clearance and/or measuring the renal clearance in the equilibrium state of one of said N-acetyl-Ser-Asp-Lys-Pro (SEQ ID NO: 1) analogs after intravascular injection, preferably single injection, of said analog.

Surprisingly, the use of these N-acetyl-Ser-Asp-Lys-Pro (SEQ ID NO: 1) analogs could make it possible, by determining the total plasma clearance (Ct), or preferably by calculating, by means of a simplified method, the value of the plasma clearance (C) according to methods known in themselves and in particular described in the articles in the names of Froissart et al. (mentioned above), to avoid fractionating urinary clearance measurements, that are more laborious to carry out in humans [but that can nevertheless be useful in animals and in the context of clinical studies] and of reducing the number of samples at some points and even at a single point, while at the same time not exhibiting the drawbacks of radiopharmaceuticals.

According to an advantageous embodiment of said method, the N-acetyl-Ser-Asp-Lys-Pro (SEQ ID NO: 1) analog is selected from the group consisting of N-acetyl-Ser($CH_2$—NH)-Asp-Lys-Pro ($S\Psi$), N-acetyl-Ser-Asp($CH_2$—NH)-Lys-Pro ($D\Psi$), N-acetyl-Ser-Asp-Lys($CH_2$—NH)-Pro ($K\Psi$) and N-acetyl-Ser-Asp-Lys-Pro-$NH_2$ (SEQ ID NO: 2).

In accordance with the invention, the measurement of the concentration of said N-acetyl-Ser-Asp-Lys-Pro (SEQ ID NO: 1) analog is carried out by any means of detection that is sensitive and specific for said analog in at least one biological sample, and in particular by immunoassay or by chromatography techniques and/or mass spectrometry techniques.

Advantageously, said immunoassay is a very specific immunoassay that cross reacts neither with the natural molecule (AcSDKP) (SEQ ID NO: 1) nor with other amidated peptides nor with converting enzyme inhibitors (Junot C. et al., J. Immunoassay Immunochem., 2001, 22, 15-31). The accuracy and the reproducibility of this technique of assaying by EIA (enzyme immunoassay) are good. Its quantification limit is 1 nM in plasma. Moreover, AcSDKP-$NH_2$ (SEQ ID NO: 2) is not degraded by the ACE present in mouse plasma (Junot C. et al., 2001, mentioned above). Its stability evaluated under the experimental conditions and the conditions for carrying out the assays is satisfactory. In addition, no adverse modification was observed after 3 freezing-thawing cycles. The coefficients of variation (CV), of repeatability and of reproducibility are between 1.4 and 186 and the exactness values are between 85 and 115% of the theoretical values (Junot C. et al., 2001, mentioned above).

Also in accordance with the invention, said N-acetyl-Ser-Asp-Lys-Pro (SEQ ID NO: 1) analog can be radiolabeled. In this case, the concentration of peptide is measured by means of an imaging technique or by radioactive counting of the samples.

A subject of the present invention is also a kit or pack for measuring glomerular filtration rate, characterized in that it comprises an N-acetyl-Ser-Asp-Lys-Pro (SEQ ID NO: 1) analog selected from the group consisting of N-acetyl-Ser ($CH_2$—NH)-Asp-Lys-Pro (SΨ), N-acetyl-Ser-Asp($CH_2$—NH)-Lys-Pro (DΨ), N-acetyl-Ser-Asp-Lys($CH_2$—NH)-Pro (KΨ) and N-acetyl-Ser-Asp-Lys-Pro-$NH_2$ (SEQ ID NO: 2), and a means of detecting said analog in at least one biological sample.

According to an advantageous embodiment of said kit or pack, said means of detecting said analog is selected from the group consisting of immunoassays, chromatography techniques and/or mass spectrometry techniques.

According to another advantageous embodiment of said kit or pack, said analog is radiolabeled and said detection means is selected from the group consisting of imaging techniques and radioactive counting techniques.

The N-acetyl-Ser-Asp-Lys-Pro (SEQ ID NO: 1) analogs satisfy the criteria for choosing an ideal marker or indicator of glomerular filtration:

they are freely filtered, they do not bind to plasma proteins, they are neither secreted, nor reabsorbed, nor metabolized by the tubule, they have no physiological effect when given as a single administration, they are devoid of toxicity and are not eliminated via any extrarenal route, they are resistant to hydrolysis by rat and human ACE, in vitro and in vivo, unlike the natural peptide.

BRIEF DESCRIPTION OF THE DRAWINGS

Besides the above provisions, the invention also comprises other provisions that will emerge from the following description, which refers to examples of implementation of the method that is the subject of the present invention, and also to the attached drawings, in which.

Figure 1:
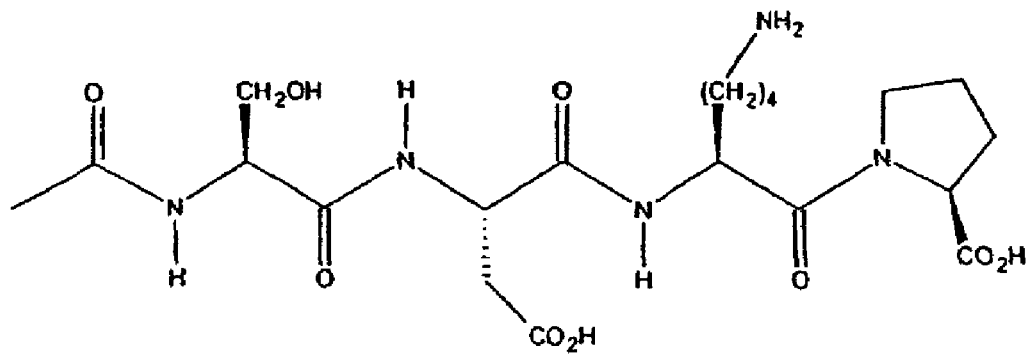
FIG. 1 represents the formulae of the N-acetyl-Ser-Asp-Lys-Pro (SEQ ID NO: 1) analogs

It should be understood, however, that these examples are given only by way of illustration of the subject of the invention, of which they in no way constitute a limitation.

EXAMPLE 1

I Materials and Methods

I.1. Products

The two peptides (ACSDKP (SEQ ID NO: 1) and AcSDKP-$NH_2$ (SEQ ID NO: 2)-97% pure) come from the company Neosysteme. The captopril and the $^3$H-inulin (95% pure—specific activity: 200 mCi/g) come from the company Sigma. Each injection solution was prepared separately in physiological saline one day before the animal experiments.

The verification of the concentration of the solutions administered and also the assaying of the samples were carried out by immunoassay, in accordance with the method disclosed in Junot C. et al., mentioned above, for the groups treated with AcSDKP (SEQ ID NO: 1) and with AcSDKP-$NH_2$ (SEQ ID NO: 2), and by liquid scintillation for the control groups treated with $^3$H-inulin (G).

The detection limit chosen for the AcSDKP (SEQ ID NO: 1) group is 0.2 nM for the plasma samples and 0.5 nM for the urine samples. For the AcSDKP-$NH_2$ (SEQ ID NO: 2) group, the detection limit is 0.15 ng/ml for the plasma and urine samples.

I.2. Animals

The study was carried out on male Wistar rats (average weight approximately 320 g) catheterized beforehand in the femoral artery. The number of rats was five per group (6 groups).

Group 1:1 mg/kg of AcSDKP (SEQ ID NO: 1) given I.V. (bolus),

Group 2: captopril (10 mg/kg/d) for 7 days by gavage, then 1 mg/kg of AcSDKP (SEQ ID NO: 1)+1 mg/kg of captopril given I.V. (bolus) on the day of the kinetics, Group 3: 1 mg/kg of AcSDKP-$NH_2$ (SEQ ID NO: 2) given I.V. (bolus), Group 4: captopril (10 mg/kg/d) for 7 days by gavage, then 1 mg/kg of AcSDKP-$NH_2$ (SEQ ID NO: 2)+1 mg/kg of captopril given I.V. (bolus) on the day of the kinetics, Group 5: 1 mg/kg of $^3$H-inulin(G) (approximately 78 μci/rat) given I.V. (bolus), Group 6: captopril (10 mg/kg/d) for 7 days by gavage, then 1 mg/kg of $^3$H-inulin(G) (approximately 60 μci/rat) given I.V. (bolus).

Protocol Deviations:

One additional rat was taken into account for Group No. 3 (AcSDKP-$NH_2$ alone) (SEQ ID NO: 2).

Doses administered: 1.20 mg/kg for AcSDKP (SEQ ID NO: 1)-0.82 mg/kg for AcSDKP-$NH_2$ (SEQ ID NO: 2)-1.05 mg/kg for $^3$H-inulin.

Urine samples: additional samples were taken for the groups (1-2-3-4-5) in order to have as large a pool of information as possible:

Group No. 1: $T_{0-2h}$-$T_{2-4h}$-$T_{4-h}$-$T_{5-24h}$-$T_{24-36h}$-$T_{36-48h}$ Group No. 2: $T_{24-30h}$-$T_{30-48h}$ Group No. 3: $T_{4-7h}$-$T_{7-24h}$-$T_{24-48h}$ Group No. 4: $T_{0-4h}$-$T_{4-24h}$-$T_{24h-48h}$-$T_{48-72h}$ Group No. 5: $T_{2-5h}$-$T_{5-7h}$-$T_{7-24h}$-$T_{24-30h}$-$T_{30-48h}$-$T_{48-72h}$ I.3. Measurements The plasma concentration of the compounds was measured at the following times: $T_0$-$T_5$-$T_{10}$-$T_{30}$-$T_{60}$-$T_{120}$-$T_{240}$-$T_{300}$ minutes.

The concentration of the compounds in the urine was measured at the following times: $T_{-24-0h}$ (before the beginning of the experiments), $T_{0-2h}$, $T_{2-4h}$, $T_{4-24h}$ and at the times described in the "Protocol deviations" section for the additional urine samples.

II Pharmacokinetic Analysis

The main pharmacokinetic parameters obtained by modeling on the Siphar V04 program (Simed, Créteil) were:

$AUC_{0-Tlast}$: area under the curve up to the last measurable point
$AUC_{0-inf}$: area under the curve to infinity
T½: elimination half-life
plasma clearance
urinary clearance: (total quantity excreted in the urine/plasma AUC)/weight of the rat.

The pharmacokinetic modeling was carried out in the following way:
two-compartment analysis for the groups treated with the $^3$H-inulin,
one-compartment analysis for the groups treated with the AcSDKP (SEQ ID NO: 1) and AcSDKP-NH$_2$ (SEQ ID NO: 2).

III Results

The concentrations in the plasma and urine measured and also the pharmacokinetic parameters modeled for each rat are presented:

| Table I | AcSDKP (SEQ ID NO: 1) | Group No. 1 |
|---|---|---|
| Table II | AcSDKP (SEQ ID NO: 1) in the presence of captopril | Group No. 2 |
| Table III | AcSDKP-NH$_2$ (SEQ ID NO: 2) | Group No. 3 |
| Table IV | AcSDKP-NH$_2$ (SEQ ID NO: 2) in the presence of captopril | Group No. 4 |
| Table V | $^3$H-inulin | Group No. 5 |
| Table VI | $^3$H-inulin in the presence of captopril | Group No. 6 |
| Table VII | Summarizing table | |

ACSDKP (SEQ ID NO: 1) is an endogenous peptide in rats. As a result, for Groups No. 1 and No. 2, the endogenous AcSDKP (SEQ ID NO: 1) had to be subtracted from the results. The amount of endogenous AcSDKP (SEQ ID NO: 1) was determined by adding up the quantity of AcSDKP (SEQ ID NO: 1) (nmol) of the period $T_{24-48h}$ (it is considered that, 24 hours after administration of the peptide given I.V., only the endogenous AcSDKP (SEQ ID NO: 1) is present). This result is multiplied by 2 (for the period $T_{0-24h}$ and $T_{24-48h}$) and subtracted from the total quantity in the urine for each rat.

Figure 2:
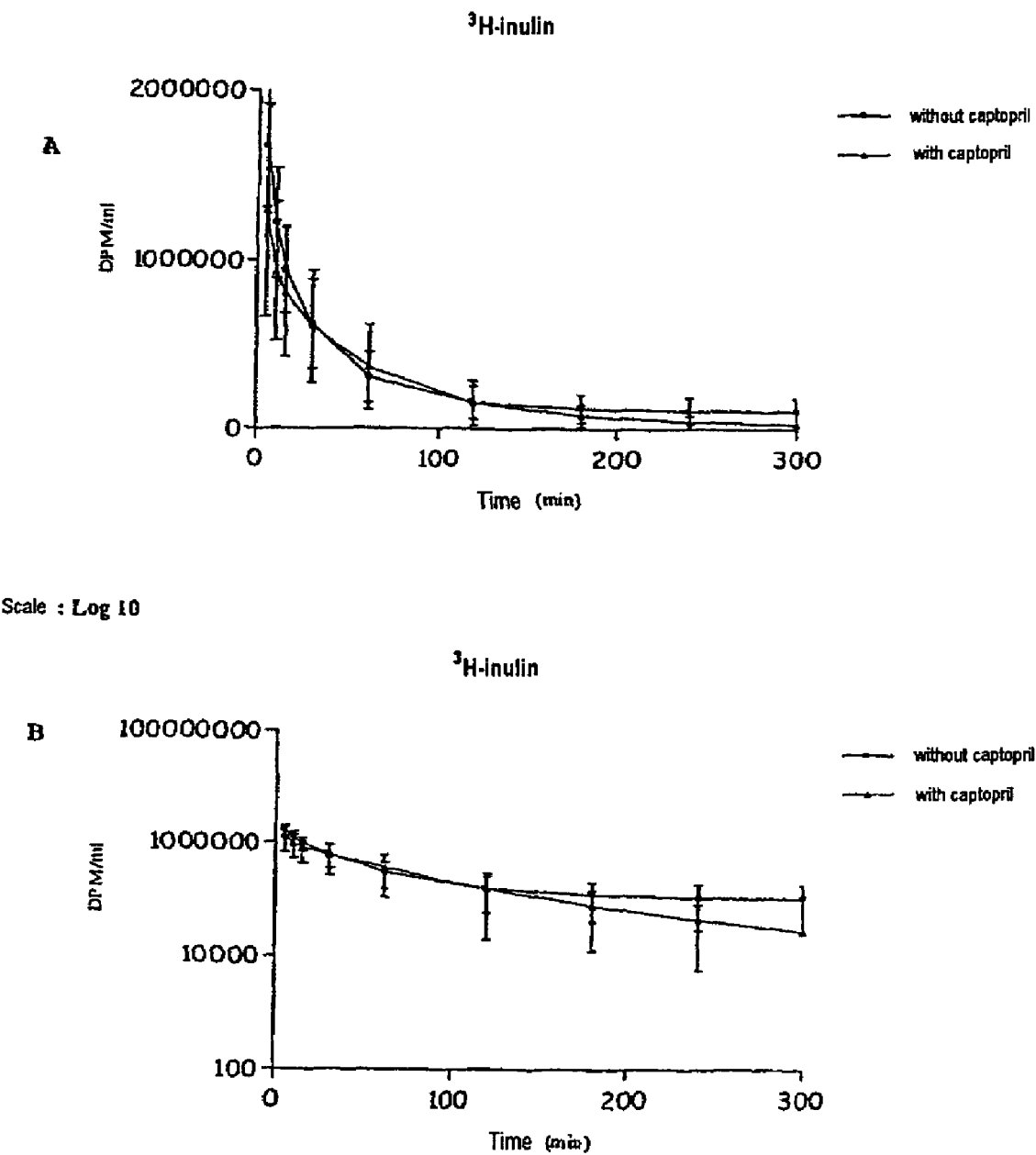
FIGS. 2A and 2B represent the plasma kinetics of inulin with and without captopril

The graphic representations of the mean concentrations in the plasma for each group are represented:

FIGS. 2A and 2B $^3$H-inulin Groups No. 5 and No. 6

Figure 3:
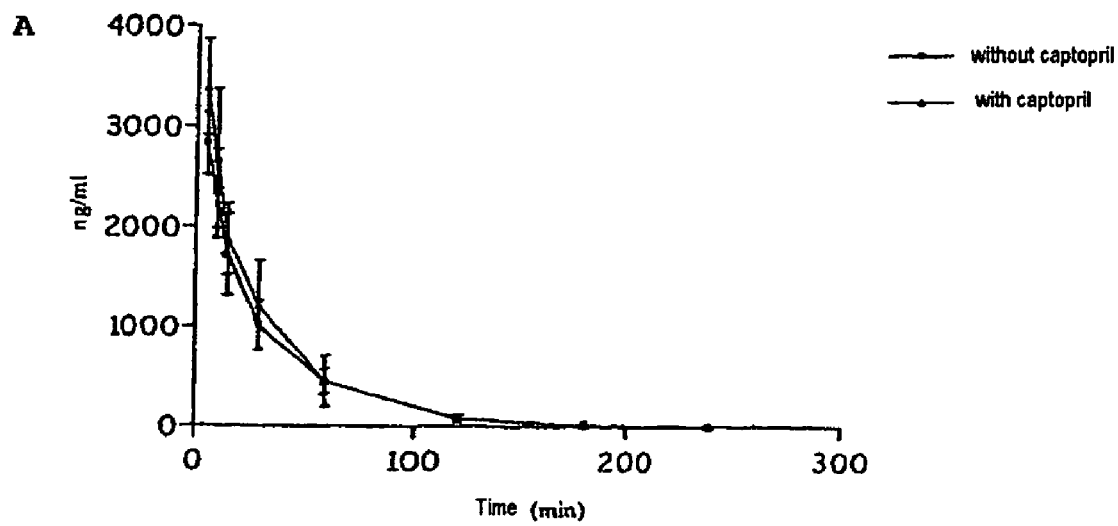
FIGS. 3A and 3B represent the plasma kinetics of the N-acetyl-Ser-Asp-Lys-Pro-$NH_2$ (SEQ ID NO: 2) analog, with and without captopril
Figure 3:
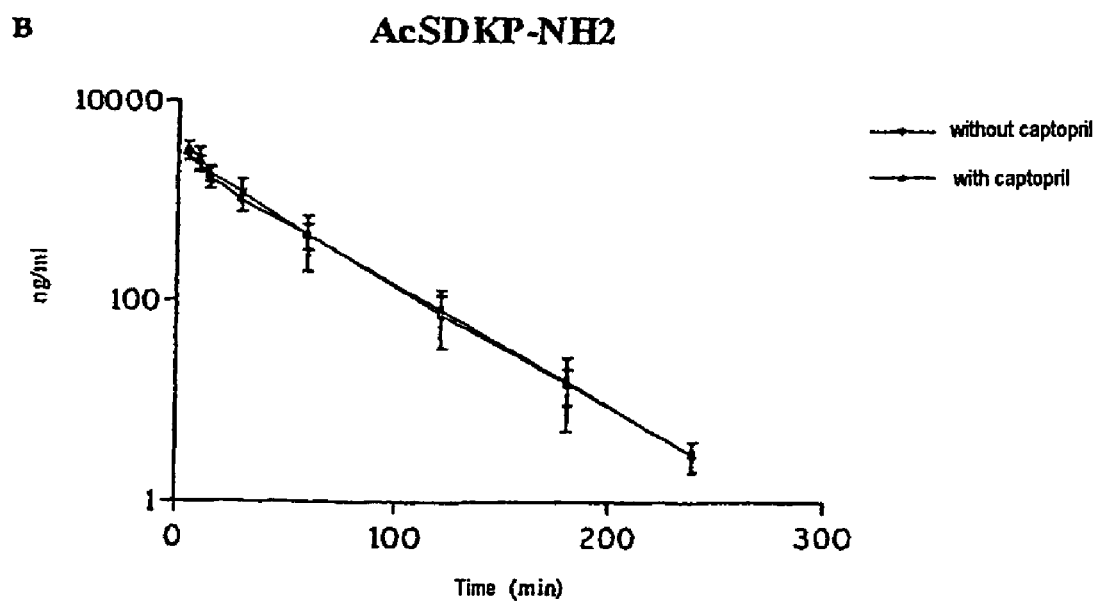

FIGS. 3A and 3B

AcSDKP-NH$_2$ (SEQ ID NO: 2) Groups No. 3 and No. 4

Figure 4:
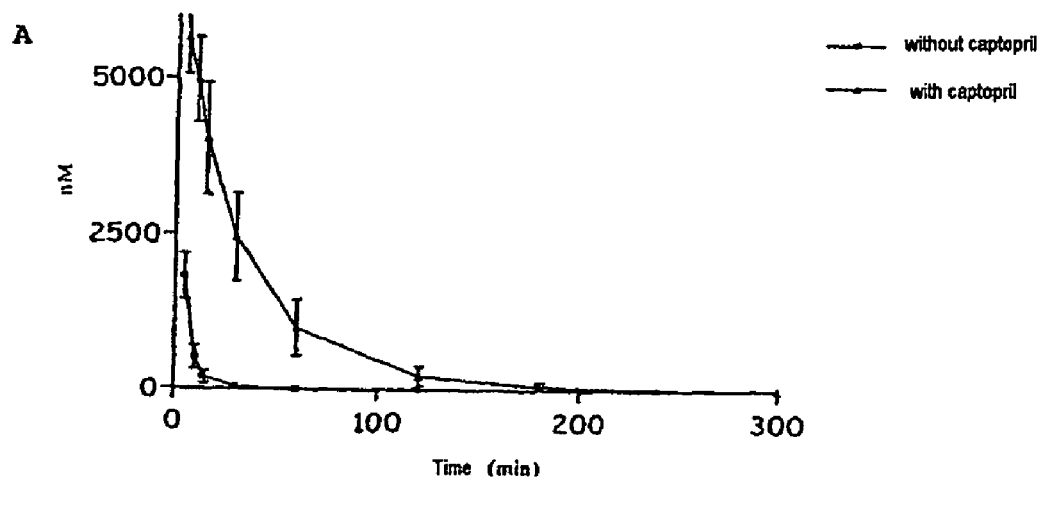
FIGS. 4A and 4B represent the plasma kinetics of the N-acetyl-Ser-Asp-Lys-Pro (SEQ ID NO: 1), with and without captopril.
Figure 4:
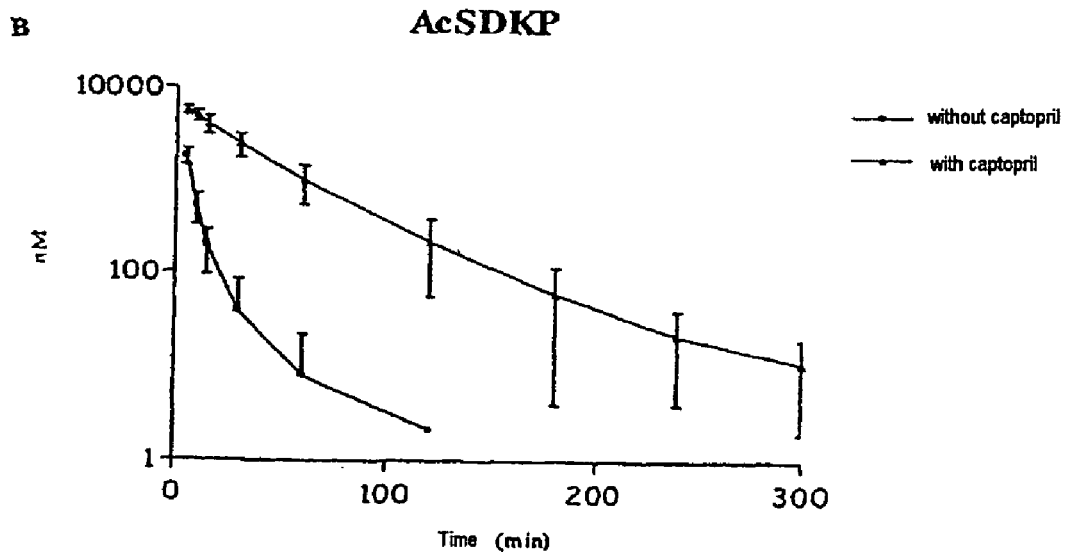

FIGS. 4A and 4B

AcSDKP (SEQ ID NO: 1) Groups No. 1 and No. 2

(AcSDKP in these Figures and the tables below corresponds to SEQ ID NO: 1 and AcSDKP-NH$_2$ corresponds to SEQ ID NO: 2.)

TABLE I

Group No. 1 - AcSDKP without captopril
Concentration in the plasma and urine and pharmacokinetic parameters for AcSDKP

| Time (min) | rats | | | | | mean | SD |
|---|---|---|---|---|---|---|---|
| | 1 | 3 | 4 | 5 | 8 | | |
| Concentration in plasma (nM) | | | | | | | |
| 5 | 2188 | 1759 | 1239 | 2100 | 1802 | 1818 | 373 |
| 10 | 729 | 400 | 265 | 671 | 508 | 514 | 191 |
| 15 | 268 | 96 | 135 | 328 | 143 | 194 | 99 |
| 30 | 34 | 14 | 10 | 121 | 10 | 38 | 47.6 |
| 60 | 5 | 0.36 | 0.15 | 33 | 2 | 8.2 | 14.2 |
| 120 | ILQ | ILQ | ILQ | 2 | ILQ | 2.2 | — |
| 180 | ILQ | ILQ | ILQ | ILQ | ILQ | — | — |
| 240 | ILQ | ILQ | ILQ | ILQ | ILQ | — | — |
| 300 | ILQ | ILQ | ILQ | ILQ | ILQ | — | — |
| $AUC_{0-inf}$ nM*min | 230401 | 16319 | 13026 | 18178 | 16223 | 17393 | 3625 |
| t½ (min) | 6.4 | 4.7 | 4.4 | 12.8 | 5.9 | 6.8 | 3.4 |
| VD (ml/kg) | 894 | 1070 | 1034 | 2600 | 1346 | 1389 | 697 |
| Concentration in urine (nM) | | | | | | | |
| 0-2 h | 22830 | NS | 27250 | 135 | NS | | |
| 2-4 h | 11810 | NS | 16220 | 14270 | NS | | |
| 4-5 h | 12050 | 14060 | NS | 7806 | NS | | |
| 5-24 h | 299 | 2494 | NS | 965 | 1334 | | |
| 21-36 h | 244 | 333 | 2697 | 93 | NS | | |
| 36-48 h | 77 | 61 | 214 | 55 | 141 | | |
| Urine volume (ml) | | | | | | | |
| 0-2 h | 1.1 | NS | 1.7 | 0.7 | NS | | |
| 2-4 h | 0.6 | NS | 1.0 | 2.5 | NS | | |
| 4-5 h | 2.8 | 3.7 | NS | 1.9 | NS | | |
| 5-24 h | 33.2 | 4.1 | NS | 21.3 | 58.9 | | |

TABLE I-continued

Group No. 1 - AcSDKP without captopril
Concentration in the plasma and urine and pharmacokinetic parameters for AcSDKP

| Time (min) | rats 1 | 3 | 4 | 5 | 8 | mean | SD |
|---|---|---|---|---|---|---|---|
| 24-36 h | 16.9 | 10.1 | 5.2 | 9 | NS | | |
| 36-48 h | 51.6 | 27.1 | 16.1 | 36.7 | 56.1 | | |
| Q in urine (nmol) | | | | | | | |
| 0-2 h | 25.1 | 0.0 | 46.7 | 0.1 | NS | | |
| 2-4 h | 7.1 | 0.0 | 15.7 | 36.4 | NS | | |
| 4-5 h | 33.5 | 51.3 | 0.0 | 14.6 | NS | | |
| 5-24 h | 9.9 | 10.2 | 0.0 | 20.6 | 78.5 | | |
| 24-36 h | 4.1 | 3.4 | 15.5 | 0.9 | NS | | |
| 36-48 h | 4.0 | 1.7 | 3.4 | 2.0 | 7.9 | | |
| total (nmol) | 83.7 | 66.6 | 81.3 | 74.5 | 86.5 | | |
| Q administered (nmol) | 757.7 | 705.5 | 771.9 | 833 | 832.0 | | |
| Weight (kg) | 0.3392 | 0.3265 | 0.3035 | 0.3210 | 0.3258 | 0.32 | 0.01 |
| Dose (mg/kg) | 1.09 | 1.05 | 1.24 | 1.27 | 1.24 | 1.18 | 0.1 |
| % excreted | 1.1 | 9.4 | 10.5 | 8.9 | 10.4 | 10.07 | 0.86 |
| % excreted - endog | 8.9 | 8.0 | 5.6 | 8.3 | 8.5 | 7.86 | 1.29 |
| $CL_R$ (ml/min/kg) | 10.7 | 12.5 | 20.3 | 12.8 | 16.4 | 14.52 | 3.82 |
| $CL_R$ (ml/min/kg)-endog | 8.6 | 11.1 | 11.5 | 11.8 | 13.0 | 11.21 | 1.61 |
| $C_{total}$ (ml/min/kg)dose/AUC | 97 | 132.6 | 192.6 | 142.8 | 157.4 | 144.46 | 34.95 |

NS: no sample

TABLE II

Group No. 2 - AcSDKP with captopril
Concentration in the plasma and urine and pharmacokinetic parameters for AcSDKP in the presence of captopril

| Time (min) | rats 1 | 2 | 6 | 7 | 8 | mean | SD |
|---|---|---|---|---|---|---|---|
| Concentration in plasma (nM) | | | | | | | |
| 5 | 6707 | 5413 | 5511 | 5293 | 5393 | 5663 | 588 |
| 10 | 5920 | 4813 | 4288 | 5439 | 4445 | 4981 | 687 |
| 15 | 5571 | 4016 | 3399 | 3876 | 3343 | 4041 | 904 |
| 30 | 3645 | 2176 | 2485 | 2173 | 1804 | 2457 | 707 |
| 60 | 1759 | 735 | 848 | 1069 | 590 | 1000 | 459 |
| 120 | 501 | 151 | 145 | 197 | 97 | 218 | 162 |
| 180 | 159 | 32 | 39 | 48 | 21 | 60 | 56 |
| 240 | 52 | 10 | 18 | 23 | 7 | 22 | 18 |
| 300 | 26 | 9 | 6 | 11 | 4 | 11 | 9 |
| AUC 0-INF nM*min | 341133 | 196456 | 200683 | 217932 | 167504 | 224742 | 67543 |
| t½ (min) | 35.5 | 29.2 | 29.5 | 31.4 | 28.1 | 30.7 | 2.9 |
| Vd(ml/kg) | 353 | 653 | 499 | 505 | 567 | 515 | 110 |
| Concentration in urine (nM) | | | | | | | |
| 0-2 h | NS | NS | NS | NS | NS | | |
| 2-4 h | 253 | 821500 | 126214 | NS | 126118 | | |
| 4-24 h | 25502 | 2119 | 7607 | 58597 | 5746 | | |
| 24-30 h | 202 | 1081 | NS | NS | NS | | |
| 30-48 h | 248 | 55 | 197 | 69 | 165 | | |
| Urine volume (ml) | | | | | | | |
| 0-2 h | NS | NS | NS | NS | NS | | |
| 2-4 h | 0.8 | 0.9 | 6.5 | NS | 4.2 | | |
| 4-24 h | 19.8 | 23.1 | 28.9 | 11.1 | 35.2 | | |
| 24-30 h | 8.2 | 8.9 | NS | NS | NS | | |
| 30-48 h | 32.4 | 44.3 | 53.9 | 6.5 | 64.4 | | |
| total | 61.1 | 77.2 | 89.2 | 17.6 | 103.9 | | |
| Q in urine (nmol) | | | | | | | |
| 0-2 h | 0.0 | 0.0 | 0.0 | 0.0 | 0.0 | | |
| 2-4 h | 0.2 | 744.4 | 820.9 | 0.0 | 535.3 | | |
| 4-6 h | 0.0 | 0.0 | 0.0 | 0.0 | 0.0 | | |
| 6-24 h | 504.6 | 49.0 | 219.7 | 649.1 | 202.3 | | |

TABLE II-continued

Group No. 2 - AcSDKP with captopril
Concentration in the plasma and urine and pharmacokinetic parameters for AcSDKP in the presence of captopril

| | rats | | | | | | |
|---|---|---|---|---|---|---|---|
| Time (min) | 1 | 2 | 6 | 7 | 8 | mean | SD |
| 24-30 h | 1.6 | 9.6 | 0.0 | 0.0 | 0.0 | | |
| 30-48 h | 8.0 | 2.5 | 10.6 | 0.4 | 10.6 | | |
| | | | | | | | |
| total (nmol) | 514.5 | 805.5 | 1051.2 | 649.5 | 748.3 | | |
| Q administered (nmol) | 657.7 | 918.1 | 739.4 | 718.9 | 764.7 | | |
| Weight (kg) | 0.2796 | 0.3017 | 0.3135 | 0.2955 | 0.3211 | 0.30 | 0.02 |
| Dose (kg) | 1.15 | 1.48 | 1.15 | 1.19 | 1.16 | 1.23 | 0.15 |
| % excreted | 78.2 | 87.7 | 142.2 | 90.4 | 97.9 | 99.27 | 25.00 |
| % excreted - endog | 75.3 | 85.1 | 139.3 | 90.2 | 95.1 | 97.00 | 24.77 |
| $CL_R$ (ml/min/kg) | 5.39 | 13.59 | 16.71 | 10.09 | 13.91 | 11.94 | 4.35 |
| $CL_R$ (ml/min/kg)-endog | 5.2 | 13.2 | 16.4 | 10.1 | 13.5 | 11.67 | 4.25 |
| $C_{total}$ (ml/min/kg)dose/AUC | 6.9 | 15.5 | 11.8 | 11.2 | 14.2 | 11.9 | 3.31 |

NS: no sample

ACSDKP in the above table corresponds to SEQ ID NO: 1.

TABLE III

Group No. 3 - AcSDKP-$NH_2$ with captopril
Concentration in the plasma and urine and pharmacokinetic parameters for AcSDKP-$NH_2$

| | rats | | | | | | | |
|---|---|---|---|---|---|---|---|---|
| Time (min) | 1 | 2 | 1a | 4 | 5 | 6 | mean | SD |
| | Concentration in plasma (ng/ml) | | | | | | | |
| 5 | 2581 | 3139 | 2865 | 2491 | 3250 | 2663 | 2831 | 309 |
| 10 | 1611 | 2288 | 2425 | 2152 | 2918 | 2595 | 2331 | 442 |
| 15 | 1655 | 985 | 2204 | 1796 | 1930 | 1750 | 1720 | 407 |
| 30 | 748 | 880 | 1317 | 1329 | 930 | 867 | 1012 | 248 |
| 60 | 233 | 443 | 598 | 545 | 416 | 463 | 450 | 126 |
| 120 | 47 | 45 | 163 | 118 | 48 | 69 | 82 | 48 |
| 180 | 6 | 8 | 25 | 32 | 9 | 19 | 16 | 11 |
| 240 | ILQ | ILQ | 3 | 5 | 2 | 4 | 3 | 1 |
| 300 | ILQ | ILQ | ILQ | ILQ | ILQ | ILQ | | |
| $AUC_{0-INF}$ ng/ml*min | 73978 | 87407 | 125025 | 111894 | 101003 | 96190 | 99249 | 17976 |
| $t^{1/2}$ (min) | 20.7 | 20.7 | 24.5 | 26.8 | 21.8 | 25.1 | 23.3 | 2.5 |
| Vd (ml/kg) | 338 | 270 | 220 | 253 | 256 | 261 | 266 | 39 |
| | Concentration in urine (ng/ml) | | | | | | | |
| 0-2 h | 41655 | NS | NS | NS | NS | NS | | |
| 2-4 h | NS | 67056 | NS | 22941 | 148362 | NS | | |
| 4-7 h | 19076 | 9228 | NS | NS | NS | NS | | |
| 7-24 h | 462 | 192 | 8467 | 965 | 815 | 6202 | | |
| 24-48 h | 10 | 42 | 986 | 16 | ILQ | 59 | | |
| | Urine volume (ml) | | | | | | | |
| 0-2 h | 4.22 | NS | NS | NS | NS | NS | | |
| 2-4 h | NS | 2.69 | NS | 6.16 | 1.96 | NS | | |
| 4-7 h | 4.41 | 2.55 | NS | NS | NS | NS | | |
| 7-24 h | 34.69 | 44.55 | 24.98 | 43.42 | 35.87 | 25.7 | | |
| 24-48 h | 53.33 | 31.19 | 47.91 | 37.26 | 64.86 | 53.41 | | |
| | Q in urine (ng) | | | | | | | |
| 0-2 h | 175685.1 | 0.0 | 0.0 | 0.0 | 0.0 | 0.0 | | |
| 2-4 h | 0.0 | 180325.8 | 0.0 | 141210.2 | 290581.1 | 0.0 | | |
| 4-7 h | 84030.9 | 23548.7 | 0.0 | 0.0 | 0.0 | 0.0 | | |
| 7-24 h | 16014.8 | 8570.5 | 211497.2 | 41898.9 | 29223.7 | 159391.7 | | |
| 24-48 h | 513.0 | 1304.8 | 47218.0 | 603.6 | ILQ | 3161.4 | | |
| | | | | | | | | |
| total (ng) | 276243.9 | 213749.7 | 258715.2 | 183712.7 | 319804.8 | 162553.1 | | |
| Q administered (ng) | 264881 | 251981 | 253401 | 246391 | 264881 | 233921.0 | | |
| Weight (kg) | 0.3162 | 0.3196 | 0.3253 | 0.3363 | 0.3221 | 0.3375 | 0.33 | 0.01 |
| Dose (mg/kg) | 0.84 | 0.79 | 0.78 | 0.73 | 0.82 | 0.69 | 0.78 | 0.05 |
| % excreted | 104.3 | 84.8 | 102.1 | 74.6 | 120.7 | 69.5 | 92.67 | 19.69 |

TABLE III-continued

Group No. 3 - AcSDKP-NH$_2$ with captopril
Concentration in the plasma and urine and pharmacokinetic parameters for AcSDKP-NH$_2$

| | rats | | | | | | | |
|---|---|---|---|---|---|---|---|---|
| Time (min) | 1 | 2 | 1a | 4 | 5 | 6 | mean | SD |
| CL$_R$ (ml/min/kg) | 11.8 | 7.7 | 6.4 | 4.9 | 9.8 | 5.0 | 7.59 | 2.77 |
| C$_{total}$ (ml/min/kg)dose/AUC | 11.3 | 9 | 6.2 | 6.5 | 8.1 | 7.2 | 8.08 | 1.89 |

NS: no sample

Where AcSDKP-NH$_2$ in the above table corresponds to SEQ ID NO: 2.

TABLE IV

Group No. 4 - AcSDKP-NH$_2$ with captopril
Concentration in the plasma and urine and pharmacokinetic parameters for AcSDKP-NH$_2$ in the presence of captopril

| | rats | | | | | | |
|---|---|---|---|---|---|---|---|
| Time (min) | 1 | 2 | 3 | 4 | 6a | mean | SD |
| *Concentration in plasma (ng/ml)* | | | | | | | |
| 5 | 3623 | 3115 | 4099 | 2863 | 3280 | 3396 | 480 |
| 10 | 1750 | 3571 | 3075 | 2682 | 2346 | 2685 | 694 |
| 15 | 1432 | 1978 | 2363 | 1635 | 1960 | 1874 | 357 |
| 30 | 1128 | 891 | 1173 | 889 | 1986 | 1213 | 452 |
| 60 | 312 | 338 | 346 | 357 | 910 | 453 | 256 |
| 120 | 31 | 63 | 64 | 73 | 140 | 74 | 40 |
| 180 | 7 | 11 | 18 | 16 | 23 | 15 | 6 |
| 240 | 2 | 3 | 3 | 3 | 2 | 3 | 0 |
| 300 | ILQ | ILQ | ILQ | ILQ | 0 | 0 | |
| AUC$_{0-INF}$ ng/ml*min | 89343 | 100543 | 114983 | 92278 | 153339 | 110097 | 26140 |
| t½ (min) | 21.9 | 23.0 | 23.1 | 24.1 | 23.3 | 23.1 | 0.8 |
| Vd(ml/kg) | 284 | 230 | 260 | 327 | 242 | 269 | 38 |
| *Concentration in urine (ng/ml)* | | | | | | | |
| 0-4 h | NS | NS | NS | NS | NS | | |
| 4-24 h | 10906 | 3107 | 11032 | 22749 | 10380 | | |
| 24-48 h | 239 | 35 | 337 | 171 | 178 | | |
| 48-72 h | 11 | ILQ | 11 | 70 | NS | | |
| *Urine volume (ml)* | | | | | | | |
| 0-4 h | 0.00 | 0.00 | 0.00 | 0.00 | 0.00 | | |
| 4-24 h | 19.12 | 46.46 | 25.93 | 12.05 | 34.09 | | |
| 24-48 h | 44.93 | 62.22 | 48.50 | 58.89 | 37.78 | | |
| 48-72 h | 70.88 | 57.86 | 58.98 | 57.25 | 0.00 | | |
| *Q in urine (ng)* | | | | | | | |
| 0-4 h | | | | | | | |
| 4-24 h | 208504.2 | 144361.5 | 286064.8 | 274157.3 | 353834.5 | | |
| 24-48 h | 10737.7 | 2183.9 | 16360.4 | 10087.6 | 6728.5 | | |
| 48-72 h | 758.4 | ILQ | 619.3 | 4008.3 | 0.0 | | |
| total (ng) | 220000 | 146545.0 | 303045 | 288253 | 360563 | | |
| Q administered (ng) | 242311 | 216121 | 259558 | 255512 | 341274 | 262955.22 | |
| Weight (kg) | 0.3009 | 0.3100 | 0.2900 | 0.2951 | 0.3092 | 0.30 | 0.01 |
| Dose (mg/kg) | 0.81 | 0.7 | 0.9 | 0.87 | 1.1 | 0.87 | 0.15 |
| % excreted | 90.8 | 67.8 | 116.8 | 112.8 | 105.7 | 98.76 | 19.94 |
| CL$_R$ (ml/min/kg) | 8.2 | 4.7 | 9.1 | 10.6 | 7.6 | 8.03 | 2.18 |
| C$_{total}$ (ml/min/kg)dose/AUC | 9.0 | 6.9 | 7.8 | 9.4 | 7.2 | 8.06 | 1.09 |

NS: no sample

Where AcSDKP-NH$_2$ in the above table corresponds to SEQ ID NO: 2.

TABLE V

Groupe No. 5 - inulin-$^3$NH without captopril
Concentration in the plasma and urine and pharmacokinetic parameters for $^3$H-inulin

| time (min) | \|  rats  \| | | | | | mean | SD |
|---|---|---|---|---|---|---|---|
| | 6 | 7 | 8 | 9 | 10 | | |
| *Concentration in plasma (DPM/ml)* | | | | | | | |
| 5 | 1.44E+06 | 2.10E+08 | 1.93E+06 | 1.67E+06 | 1.21E+06 | 1.67E+06 | 3.60E+05 |
| 10 | 1.31E+06 | 1.62E+06 | 1.38E+06 | 1.01E+06 | 7.85E+05 | 1.22E+06 | 3.25E+08 |
| 15 | 1.15E+06 | 1.14E+06 | 1.07E+06 | 7.84E+05 | 5.65E+05 | 9.41E+05 | 2.57E+05 |
| 30 | 9.86E+05 | 7.67E+05 | 6.05E+05 | 3.95E+05 | 3.38E+05 | 6.18E+05 | 2.67E+05 |
| 60 | 5.00E+05 | 4.03E+05 | 2.97E+05 | 1.58E+05 | 1.64E+05 | 3.04E+05 | 1.49E+05 |
| 120 | 2.52E+05 | 2.19E+05 | 1.98E+05 | 5.80E+04 | 4.33E+04 | 1.54E+05 | 9.65E+04 |
| 180 | 1.94E+05 | 1.77E+05 | 1.71E+05 | 4.17E+04 | 2.45E+04 | 1.21E+05 | 8.13E+04 |
| 240 | 1.72E+05 | 1.59E+05 | 1.74E+05 | 2.76E+04 | 1.56E+04 | 1.09E+05 | 8.06E+04 |
| 300 | 1.55E+05 | 1.78E+05 | 1.57E+05 | 2.25E+04 | 1.38E+04 | 1.05E+05 | 8.01E+04 |
| $AUC_{0-inf}$-DPM/ml*min | 1.75E+08 | 1.47E+08 | 1.64E+08 | 5.40E+07 | 4.22E+07 | 1.16E+08 | 6.34E+07 |
| $t\frac{1}{2}$ B (min) | 264.4 | 136.8 | 295.6 | 69.7 | 52.5 | 163.8 | 111.2 |
| $t\frac{1}{2}$ A (min) | 23.9 | 7.4 | 11.0 | 7 | 5.2 | 10.9 | 7.5 |
| Vd(ml/kg) | 1221 | 796 | 1450 | 824 | 707 | 1.00E+03 | 3.20E+02 |
| $AUC_{0-300\,min}$-DPM*min | 1.16E+08 | 1.12E+08 | 9.75E+07 | 5.17E+07 | 4.11E+07 | 8.36E+07 | 3.48E+07 |
| *Concentration in urine (DPM/ml)* | | | | | | | |
| 0-2 h | 1.63E+07 | 4.44E+07 | NS | NS | 1.55E+07 | | |
| 2-5 h | 1.51E+07 | 1.38E+07 | 3.26E+07 | NS | 9.66E+06 | | |
| 5-7 h | 1.22E+07 | 8.00E+05 | 1.05E+07 | NS | NS | | |
| 7-24 h | 1.44E+05 | 2.24E+05 | 5.00E+05 | 6.78E+06 | 4.12E+05 | | |
| 24-30 h | 3.54E+05 | 1.56E+05 | 1.92E+05 | 9.42E+05 | 5.08E+04 | | |
| 30-48 h | 1.13E+05 | 1.02E+05 | 1.12E+05 | 1.80E+04 | 2.25E+04 | | |
| 48-72 h | 6.94E+04 | 7.03E+04 | 8.60E+04 | NS | NS | | |
| *Urine volume (ml)* | | | | | | | |
| 0-2 h | 0.96 | 2.61 | NS | NS | 3.24 | | |
| 2-5 h | 7.54 | 1.58 | 4.59 | NS | 4.49 | | |
| 5-7 h | 2.84 | 2.27 | 1.23 | NS | NS | | |
| 7-24 h | 40.08 | 44.14 | 30.53 | 16.3 | 24.03 | | |
| 24-30 h | 5.27 | 8.61 | 5.32 | 5.99 | 14.76 | | |
| 30-48 h | 41.58 | 41.16 | 31.8 | 19.06 | 48.87 | | |
| 48-72 h | 61.46 | 58.63 | 46.55 | NS | NS | | |
| *Q in urine (DPM)* | | | | | | | |
| 0-2 h | 1.56E+07 | 1.16E+08 | 0.00E+00 | 0.00E+00 | 5.03E+07 | | |
| 2-5 h | 1.14E+08 | 2.18E+07 | 1.50E+08 | 0.00E+00 | 4.34E+07 | | |
| 5-7 h | 3.45E+07 | 1.81E+06 | 1.28E+07 | 0.00E+00 | 0.00E+00 | | |
| 7-24 h | 5.78E+06 | 9.87E+06 | 1.53E+07 | 1.11E+08 | 9.89E+06 | | |
| 24-30 h | 1.87E+06 | 1.35E+06 | 1.02E+07 | 5.64E+06 | 7.50E+05 | | |
| 30-48 h | 4.69E+06 | 4.22E+06 | 3.55E+06 | 3.43E+05 | 1.10E+06 | | |
| 48-72 h | 4.26E+06 | 4.12E+06 | 4.00E+06 | 0.00E+00 | 0.00E+00 | | |
| Total(DPM) | 1.81E+08 | 1.59E+08 | 1.86E+08 | 1.17E+08 | 1.05E+08 | | |
| Q administered (DPM) | 1.77E+08 | 1.90E+08 | 1.96E+08 | 1.49E+08 | 1.27E+08 | | |
| Weight (kg) | 0.3162 | 0.3196 | 0.3507 | 0.3363 | 0.3221 | 0.33 | 0.01 |
| Dose (mg/kg) | 0.93 | 1.04 | 1.05 | 1.12 | 0.87 | 1.00 | 0.1 |
| % excreted | 102.0 | 83.9 | 94.9 | 78.4 | 83 | 88.44 | 9.70 |
| $CL_{R(0inf)}$ (ml/min/kg) | 3.3 | 3.4 | 3.2 | 6.4 | 7.8 | 4.81 | 2.13 |
| $CLR_{(0-300\,min)}$ (ml/min/kg) | 4.9 | 4.5 | 5.4 | 6.7 | 8 | 5.9 | 1.42 |
| $C_{total}$ (ml/min/kg)dose/AUC | 3.2 | 4 | 3.4 | 8.2 | 9.4 | 5.64 | 2.91 |

NS: no sample

TABLE VI

Group No. 6 - Inulin-$^3$NH with captopril
Concentration in the plasma and urine and pharmacokinetic parameters for $^3$H-inulin in the presence of captopril

| Time (min) | \|  rats  \| | | | | | mean | SD |
|---|---|---|---|---|---|---|---|
| | 1 | 2 | 3 | 4 | 5 | | |
| *Concentration in plasma (DPM/ml)* | | | | | | | |
| 5 | 1.64E+06 | 2.14E+06 | 8.72E+05 | 1.26E+06 | 5.51E+05 | 1.29E+06 | 6.26E+05 |
| 10 | 9.19E+05 | 1.64E+06 | 6.67E+05 | 7.82E+05 | 6.47E+05 | 9.32E+05 | 4.12E+05 |

TABLE VI-continued

Group No. 6 - Inulin-³NH with captopril
Concentration in the plasma and urine and pharmacokinetic
parameters for ³H-inulin in the presence of captopril

| Time (min) | rats | | | | | mean | SD |
|---|---|---|---|---|---|---|---|
| | 1 | 2 | 3 | 4 | 5 | | |
| 15 | 7.16E+05 | 1.48E+06 | 5.84E+05 | 6.32E+05 | 6.15E+05 | 8.06E+05 | 3.82E+05 |
| 30 | 3.94E+05 | 1.15E+06 | 4.20E+05 | 3.62E+05 | 6.93E+05 | 6.04E+05 | 3.34E+05 |
| 60 | 1.64E+05 | 7.41E+05 | 2.52E+05 | 1.58E+05 | 5.02E+05 | 3.63E+05 | 2.53E+05 |
| 120 | 4.97E+04 | 3.67E+05 | 1.08E+05 | 4.60E+04 | 1.89E+05 | 1.52E+05 | 1.33E+05 |
| 180 | 4.21E+04 | 1.94E+05 | 6.79E+04 | 2.61E+04 | 6.34E+04 | 7.87E+04 | 6.66E+04 |
| 240 | 2.20E+04 | 1.09E+05 | 2.18E+04 | 2.06E+04 | 4.46E+04 | 4.36E+04 | 3.80E+04 |
| 300 | 2.53E+04 | 2.95E+04 | 2.24E+04 | 1.66E+04 | 4.25E+04 | 2.73E+04 | 9.71E+03 |
| $AUC_{0-inf}$-DPM/ml*min | 5.25E+07 | 1.47E+08 | 5.16E+07 | 4.38E+07 | 8.40E+07 | 7.57E+07 | 4.26E+07 |
| $t^{1/2}$ B (min) | 69.9 | 54.4 | 60.6 | 62.7 | 207.8 | 91.1 | 65.5 |
| $T^{1/2}$ A (min) | 6.4 | 2.2 | 7.7 | 7.1 | 54.9 | 16.7 | 22 |
| Vd (ml/kg) | 952 | 283 | 883 | 886 | 1732 | 9.47E+02 | 5.16E+02 |
| $AUC_{0-300\,min}$-DPM*min | 4.99E+07 | 1.45E+08 | 4.96E+07 | 4.23E+07 | 7.05E+07 | 7.14E+07 | 4.22E+07 |
| Concentration in urine (DPM/ml) | | | | | | | |
| 0-2 h | 7.81E+07 | NS | 3.77E+07 | NS | NS | | |
| 2-4 h | 8.16E+06 | NS | 1.92E+07 | NS | NS | | |
| 4-24 h | 8.83E+04 | 3.66E+06 | 4.48E+04 | 1.72E+06 | 3.76E+07 | | |
| Urine volume (ml) | | | | | | | |
| 0-2 h | 1.50 | NS | 1.75 | NS | NS | | |
| 2-4 h | 2.7 | NS | 2.75 | NS | NS | | |
| 4-24 h | 19.50 | 39.00 | 52.00 | 52.00 | 3.00 | | |
| Q in urine (DPM) | | | | | | | |
| 0-2 h | 1.17E+08 | 0.00E+00 | 6.60E+07 | 0.00E+00 | 0.00E+00 | | |
| 2-4 h | 2.20E+07 | 0.00E+00 | 5.28E+07 | 0.00E+00 | 0.00E+00 | | |
| 4-24 h | 1.33E+06 | 1.43E+08 | 2.33E+06 | 8.93E+07 | 1.13E+08 | | |
| total(DPM) | 1.40E+08 | 1.43E+08 | 1.21E+08 | 8.93E+07 | 1.13E+08 | | |
| Q administered (DPM) | 1.50E+08 | 1.60E+08 | 1.58E+08 | 1.37E+08 | 1.51E+08 | | |
| Weight (kg) | 0.3030 | 0.3016 | 0.3043 | 0.3185 | 0.3111 | 0.31 | 0.01 |
| Dose (mg/kg) | 1.12 | 1.19 | 1.17 | 0.97 | 1.09 | 1.11 | 0.09 |
| % excreted | 93.5 | 89.3 | 76.4 | 65.3 | 74.7 | 79.84 | 11.46 |
| $CL_{R-0-inf}$ (ml/min/kg) | 8.8 | 3.2 | 7.7 | 6.4 | 4.3 | 6.10 | 2.33 |
| $CL_{R(0-300\,min)}$ (ml/min/kg) | 9.3 | 3.3 | 8 | 6.6 | 5.1 | 6.47 | 2.36 |
| $C_{total}$ (ml/min/kg) | 9.5 | 3.6 | 10.1 | 9.8 | 5.8 | 7.75 | 2.9 |

NS: no sample

TABLE VII

Summarizing Table

| | AcSDKP (SEQ ID NO: 1) without captopril | AcSDKP (SEQ ID NO: 1) with captopril | AcSDKP-NH₂ (SEQ ID NO: 2) without captopril | AcSDKP-NH₂ (SEQ ID NO: 2) with captopril | ³H inulin without captopril | ³H inulin with captopril |
|---|---|---|---|---|---|---|
| % excreted | 10 | 99 | 93 | 99 | 88 | 80 |
| T ½ life (min) | 6.8 | 30.7 | 23.3 | 23.1 | 10.9 (α) 163.8 (β) | 15.7 (α) 91.1 (β) |
| Renal clearance (ml/min/kg) | 11.2 | 11.7 | 7.6 | 8.0 | 5.9 | 6.47 |
| Total clearance (ml/min/kg) | 144.4 | 11.9 | 8.1 | 8.1 | 5.6 | 7.7 |

IV Conclusions

According to the data from the literature, the renal clearance in rats is between 5 and 10 ml/min/kg (Woods, 1998: 10 ml/min/kg—Lin, 1995: 8.07 ml/min/kg—Davies, 1993: 5.2 ml/min/kg).

The mean percentages of ³H-inulin found in the urine for the control groups are 88.44% (without captopril) and 79.84% (with captopril). These values demonstrate that (to within the errors of measurement), the ³H-inulin is completely excreted and that its elimination has not been modified by the administration of captopril. The mean renal clearances are 5.90 ml/min/kg (without captopril) and 6.47 ml/min/kg (with captopril). The control groups validate the system used (animal system).

The mean percentages of AcSDKP (SEQ ID NO: 1) found in the urine for Groups No. 1 and No. 2 are 7.86% (without captopril) and 97% (with captopril). These values demonstrate that the AcSDKP (SEQ ID NO: 1) is protected by the converting enzyme inhibitor (captopril) and that, in the absence of captopril, the AcSDKP (variant SEQ ID NO: 1) is rapidly degraded in vivo. The mean renal clearances are 11.21 ml/min/kg (without captopril) and 11.67 ml/min/kg (with captopril).

The mean percentages of AcSDKP-NH$_2$ (SEQ ID NO: 2) found in the urine for Groups No. 3 and No. 4 are 92.67% (without captopril) and 98.76% (with captopril). They are not therefore modified by the administration of captopril. The mean of the area under the curve (AUC) for AcSDKP-NH$_2$ (SEQ ID NO: 2) for the group treated without captopril is approximately 10% less with respect to the mean of the concentration in the plasma of the group treated with captopril (it should be noted that the mean injected dose for the group treated in the presence of captopril is 11% higher than the group treated without captopril). The mean renal clearances are 7.59 ml/min/kg (without captopril) and 8.03 ml/min/kg (with captopril). The mean ½-life time of the peptide is 23.3 minutes for the group treated without captopril and 23.1 minutes for the group treated with captopril.

The GFR measured after administration of [$^3$H]-inulin or of AcSDKP-NH$_2$ (SEQ ID NO: 2) does not differ significantly between the various groups of rats.

EXAMPLE 2

Comparative Study of the Degradation of the Two Peptides In Vitro in the Presence of Animal and Human Converting Enzyme The peptides (100 nM) were incubated with ground rat lung material (at 0.1 mg/ml) or human converting enzyme (5 mU final concentration) in the presence or absence of captopril (10 µM final concentration) in 0.1 M Tris/HCl buffer+0.3 mM NaCl, pH=7.5. A control comprising only the peptides in the presence of 0.1 M Tris/HCl buffer+0.3 mM NaCl, pH=7.5, was carried out.

The incubations were: $T_{0\ min}$-$T_{30\ min}$-$T_{60\ min}$-$T_{120\ min}$-$T_{240\ min}$ (a time $T_{24}$ hours was realized for AcSDKP-NH$_2$ (SEQ ID NO: 2)).

A methanol extraction was carried out in order to stop the reaction. At each time, the concentration of the nondegraded peptide was measured by enzyme immunoassay.

The results were expressed as percentage of peptide assayed relative to the control for each sample time.

TABLE VIII

Results of the in vitro degradation of AcSDKP (SEQ ID NO: 1) and of AcSDKP-NH$_2$ (SEQ ID NO: 1) in the presence of rat lung ACE

| Incubation time (min) | AcSDKP (SEQ ID NO: 1) | AcSDKP (SEQ ID NO: 1) + captopril | AcSDKP-NH$_2$ (SEQ ID NO: 2) | AcSDKP-NH$_2$ (SEQ ID NO: 2) + captopril |
|---|---|---|---|---|
| $T_{30\ min}$ (1/1) | 28% | 129% | 100% | 125% |
| $T_{60\ min}$ (1/1) | 9% | 111% | 65% | 65% |
| $T_{120\ min}$ (1/1) | 5% | 75% | 95% | 109% |
| $T_{240\ min}$ (1/1) | 5% | 89% | 126% | 136% |

TABLE IX

Results of the in vitro degradation of AcSDKP (SEQ ID NO: 1) and of AcSDKP-NH$_2$ (SEQ ID NO: 2) in the presence of human ACE

| Incubation time (min) | AcSDKP (SEQ ID NO: 1) | AcSDKP (SEQ ID NO: 1) + captopril | AcSDKP-NH$_2$ (SEQ ID NO: 2) | AcSDKP-NH$_2$ (SEQ ID NO: 2) + captopril |
|---|---|---|---|---|
| $T_{10\ min}$ (1/1) | 82% | 90% | 79% | 90% |
| $T_{30\ min}$ (1/1) | 75% | 100% | 100% | 162% |
| $T_{60\ min}$ (1/1) | 50% | 85% | 116% | 78% |
| $T_{120\ min}$ (1/1) | 25% | 85% | 116% | 95% |
| $T_{240\ min}$ (1/1) | 7% | 100% | 107% | 104% |
| $T_{1440\ min}$ (1/1) | — | — | 86% | 117% |

— not carried out.

In view of these results, it may be concluded that AcSDKP-NH$_2$ (SEQ ID NO: 2) is not degraded in vivo in rats, either by ACE or by other enzyme systems, and that it is completely excreted in the urine without being reabsorbed or secreted. The curve for decrease as a function of time, the elimination half-life and the urinary clearance of AcSDKP-NH$_2$ (SEQ ID NO: 2) are not influenced by the co-administration of captopril, confirming that the peptide is not degraded by ACE in vivo.

These results show that ACSDKP (SEQ ID NO: 1) is degraded by rat ACE or ACE of human origin, and that this degradation is inhibited in the presence of captopril.

Conversely, AcSDKP-NH$_2$ (SEQ ID NO: 2) does not appear to be degraded by rat converting enzyme or converting enzyme of human origin. In fact, the concentrations found are 100±25%, i.e. within the variability limits of the assay.

The invention claimed is:

1. Kit or pack for measuring glomerular filtration rate, characterized in that it comprises:
   a radiolabelled N-acetyl-Ser-Asp-Lys-Pro (SEQ ID NO: 1) peptide analog selected from the group consisting of:
   N-acetyl-Ser(CH$_2$—NH)-Asp-Lys-Pro (SΨ),
   N-acetyl-Ser-Asp(CH$_2$—NH)-Lys-Pro (DΨ),
   N-acetyl-Ser-Asp-Lys(CH$_2$—NH)-Pro (KΨ) and
   N-acetyl-Ser-Asp-Lys-Pro-NH$_2$ (SEQ ID NO: 2); and
   at least one reagent for detecting said peptide analog in a biological sample using an immunoassay, chromatography, or mass spectrometry technique.

2. A method for calculating the glomerular filtration rate in a subject, comprising the steps:
   a) intravascular injection of a tracer comprising an ACE-resistant N-acetyl-Ser-Asp-Lys-Pro (SEQ ID NO: 1) analog selected from the group consisting of: pseudopeptides, in which one of the peptide bonds in SEQ ID NO: 1 has been replaced with an aminomethylene Ψ (CH$_2$—NH) group; and SEQ ID NO: 1 modified at its C-terminal end by amidation;
   b) measuring at least one time point subsequent to step a) at least one of the following:
      i. the concentration of said ACE-resistant N-acetyl-Ser-Asp Lys-Pro (SEQ ID NO: 1) analog in a plasma sample from said subject;
      ii. the concentration of said ACE-resistant N-acetyl-Ser-Asp-Lys-Pro (SEQ ID NO. 1) analog in a urine sample from said subject; and
   c) calculating the glomerular filtration rate based upon the measured concentration of said ACE-resistant N-acetyl-Ser-Asp-Lys-Pro (SEQ ID NO: 1) analog in step b) (i) or b) (ii).

3. The method of claim 2, wherein said analog has the following formula:
   N-acetyl-Ser(CH$_2$—NH)-Asp-Lys-Pro: SΨ
   N-acetyl-Ser-Asp(CH$_2$—NH)-Lys-Pro: DΨ
   N-acetyl-Ser-Asp-Lys(CH$_2$—NH)-Pro: KΨ or
   N-acetyl-Ser-Asp-Lys-Pro-NH$_2$ (SEQ ID NO: 2).

4. The method of claim 2, wherein said analog is radiolabelled.

5. The method of claim 2, wherein said analog is a pseudopeptide in which one of the peptide bonds has been replaced with an aminomethylene Ψ (CH$_2$—NH) group.

6. The method of claim 2, wherein said analog is a peptide modified at its C-terminal end by amidation.

7. The method of claim 2, comprising:
   measuring the concentration of said ACE-resistant N-acetyl-Ser-Asp-Lys-Pro (SEQ ID NO: 1) analog in a plasma sample from said subject.

8. The method of claim 2, comprising:
   measuring the concentration of said ACE-resistant N-acetyl-Ser-Asp-Lys-Pro (SEQ ID NO: 1) analog in a urine sample from said subject.

9. The kit or pack of claim 1 that comprises radiolabelled N-acetyl-Ser(CH$_2$—NH)-Asp-Lys-Pro (SΨ).

10. The kit or pack of claim 1 that comprises radiolabelled N-acetyl-Ser-Asp(CH$_2$—NH)-Lys-Pro (DΨ).

11. The kit or pack of claim 1 that comprises radiolabelled N-acetyl-Ser-Asp-Lys(CH$_2$—NH)-Pro (KΨ).

12. The kit or pack of claim 1 that comprises radiolabelled N-acetyl-Ser-Asp-Lys-Pro-NH$_2$ (SEQ ID NO: 2).

13. The kit or pack of claim 1 that comprises a reagent for detecting said analog using an immunoassay.

14. The kit or pack of claim 1 that comprises a reagent for detecting said analog using chromatography or a mass spectrometry technique.

* * * * *